US010980605B2

(12) United States Patent
Hashimoto et al.

(10) Patent No.: US 10,980,605 B2
(45) Date of Patent: Apr. 20, 2021

(54) REMOTE CONTROL ROBOT SYSTEM

(71) Applicant: KAWASAKI JUKOGYO KABUSHIKI KAISHA, Kobe (JP)

(72) Inventors: Yasuhiko Hashimoto, Kobe (JP); Nobuyasu Shimomura, Kobe (JP); Tsuyoshi Maehara, Itami (JP); Masayuki Kamon, Akashi (JP)

(73) Assignee: KAWASAKI JUKOGYO KABUSHIKI KAISHA, Kobe (JP)

(*) Notice: Subject to any disclaimer, the term of this patent is extended or adjusted under 35 U.S.C. 154(b) by 192 days.

(21) Appl. No.: 15/755,115

(22) PCT Filed: May 27, 2016

(86) PCT No.: PCT/JP2016/002575
§ 371 (c)(1),
(2) Date: Feb. 26, 2018

(87) PCT Pub. No.: WO2017/033351
PCT Pub. Date: Mar. 2, 2017

(65) Prior Publication Data
US 2018/0243897 A1 Aug. 30, 2018

(30) Foreign Application Priority Data

Aug. 25, 2015 (JP) .............................. JP2015-165479

(51) Int. Cl.
A61B 34/00 (2016.01)
A61B 34/37 (2016.01)
(Continued)

(52) U.S. Cl.
CPC .............. A61B 34/37 (2016.02); A61B 34/32 (2016.02); B23P 19/04 (2013.01); B23Q 15/12 (2013.01);
(Continued)

(58) Field of Classification Search
CPC ...... A61B 4/37; A61B 34/32; G05B 19/4182; G06T 7/62; G06T 7/70; B25J 9/0081;
(Continued)

(56) References Cited

U.S. PATENT DOCUMENTS 5,833,656 A 11/1998 Smith et al.
7,724,380 B2 * 5/2010 Horita .................... G06T 7/579
235/437
(Continued)

FOREIGN PATENT DOCUMENTS

CN 104688347 A 6/2015
EP 0776739 A2 6/1997
(Continued)

OTHER PUBLICATIONS

JPO English Translation for JP04275887 (Year: 1992).*
(Continued)

Primary Examiner — Ian Jen
(74) Attorney, Agent, or Firm — Oliff PLC

(57) ABSTRACT

A remote control robot system includes a slave arm, a master main body imitating the shape of an object handled by the slave arm, a manipulation receiving device configured to receive manipulation of an operator based on the position and posture of the master main body, and a control device configured to control operation of the slave arm based on the manipulation received by the manipulation receiving device so that behavior of the object corresponds to behavior of the master main body.

8 Claims, 6 Drawing Sheets

(51) Int. Cl.
| | |
|---|---|
| G05B 19/418 | (2006.01) |
| B25J 9/00 | (2006.01) |
| B25J 9/16 | (2006.01) |
| B23P 19/04 | (2006.01) |
| B25J 13/00 | (2006.01) |
| B25J 19/04 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ...... B25J 9/1646; B25J 9/1653; B25J 9/1674; B25J 9/1612; B25J 19/028; B25J 9/1602; B25J 13/085; B25J 13/087; B25J 9/0084; B25J 9/1697; B25J 13/006; B25J 13/08; B25J 9/0087; B25J 3/00; B25J 9/1669; B25J 13/06; B25J 13/088; B25J 18/00; B25J 9/161; B25J 9/1664; B25J 9/1682; B25J 9/1689; B25J 19/023; B25J 3/04; B25J 9/1633; B25J 9/1628; B25J 13/02; B25J 9/163; B25J 11/008; B25J 13/003; B25J 13/065; B25J 13/025; B23Q 15/12; G06F 3/017

See application file for complete search history.

(56) References Cited

U.S. PATENT DOCUMENTS

| | | | | |
|---|---|---|---|---|
| 9,126,337 | B2* | 9/2015 | Iwatake | B25J 9/1694 |
| 9,519,736 | B2* | 12/2016 | Atohira | B25J 9/1671 |
| 2006/0269123 | A1* | 11/2006 | Horita | G06T 7/579 |
| | | | | 382/154 |
| 2007/0213874 | A1* | 9/2007 | Oumi | B25J 9/1697 |
| | | | | 700/245 |
| 2008/0300723 | A1* | 12/2008 | Ban | B25J 9/1692 |
| | | | | 700/259 |
| 2008/0301072 | A1* | 12/2008 | Nagatsuka | B25J 9/1671 |
| | | | | 706/12 |
| 2013/0293701 | A1* | 11/2013 | Tani | G01C 11/02 |
| | | | | 348/135 |
| 2014/0114481 | A1 | 4/2014 | Ogawa et al. | |
| 2014/0316573 | A1* | 10/2014 | Iwatake | B25J 9/1697 |
| | | | | 700/258 |
| 2015/0157411 | A1 | 6/2015 | Choi | |
| 2015/0182289 | A1* | 7/2015 | Itkowitz | B25J 13/084 |
| | | | | 606/130 |
| 2016/0059407 | A1* | 3/2016 | Sonoda | B25J 9/0081 |
| | | | | 700/260 |
| 2016/0354933 | A1* | 12/2016 | Sato | B25J 9/1633 |
| 2017/0014995 | A1* | 1/2017 | Kato | B25J 9/1633 |
| 2017/0028550 | A1* | 2/2017 | Terada | B25J 9/162 |
| 2017/0028561 | A1* | 2/2017 | Yamada | B25J 13/082 |
| 2017/0090431 | A1* | 3/2017 | Komatsu | G05B 13/0265 |
| 2017/0270631 | A1* | 9/2017 | Melikian | B25J 9/1687 |
| 2017/0348853 | A1* | 12/2017 | Chang | G05B 19/042 |
| 2017/0368687 | A1* | 12/2017 | Huang | B25J 9/1612 |

FOREIGN PATENT DOCUMENTS

| | | |
|---|---|---|
| JP | H04-275887 A | 10/1992 |
| JP | H07-194609 A | 8/1995 |
| JP | H09-76063 A | 3/1997 |
| JP | 2003-311661 A | 11/2003 |
| JP | 2013-017513 A | 1/2013 |
| JP | 2015-071206 A | 4/2015 |
| JP | 2016-047591 A | 4/2016 |

OTHER PUBLICATIONS

US-20160059407-A1 Illustrated Figure 9; Year: Mar. 2016 (Year: 2016).*

(56) References Cited

OTHER PUBLICATIONS

Apr. 3, 2019 European Search Report issued in European Patent Application No. 16838703.3.
Aug. 16, 2016 International Search Report issued in Patent Application No. PCT/JP2016/002575.
Feb. 27, 2018 International Preliminary Report on Patentability issued in Patent Application No. PCT/JP2016/002575.
May 31, 2017 Taiwanese Office Action and Search Report issued in Taiwan Patent Application No. 105126751.

* cited by examiner

# REMOTE CONTROL ROBOT SYSTEM

TECHNICAL FIELD

The present disclosure relates to a remote control robot system provided with a master device and a slave arm.

BACKGROUND ART

Conventionally, remote control robot systems provided with a master device (i.e., a remote control device) and a slave arm which operates according to manipulation of the master device are known. As the master device, a manipulator, a control lever, a manual operation button, etc. may be used. In such remote control robot systems, some are configured so that the posture of the slave arm follows the posture of the manipulator as the master device. Patent Document 1 discloses this kind of art.

In Patent Document 1, a master-slave type manipulator for medical use, which is provided with a portable arm manipulating part as the master device is disclosed. This portable arm manipulating part includes an operation table with a shoulder belt for an operator, a display provided to the operation table, and a plurality of small master arms provided to the operation table. Tip-end parts of these master operation arms are provided with gripping forceps corresponding to gripping forceps provided to tip-end parts of surgical tools which are manipulated by the master arms, respectively.

REFERENCE DOCUMENT OF CONVENTIONAL ART

Patent Document

[Patent Document 1] JP1995-194609A

DESCRIPTION OF THE DISCLOSURE

Problems to be Solved by the Disclosure

Although the art disclosed in Patent Document 1 relates to the manipulator for medical use, if this art is applied to a handling robot, a person skilled in the art may arrive at attaching end effectors corresponding to end effectors for handling (e.g., robot hands etc.) attached to the hand parts of the slave arms, to the hand parts of the master arms.

SUMMARY OF THE DISCLOSURE

However, even if the operator manipulates the master arm or the robot hand attached to the hand part of the master arm as described above, the handling feel of an object is poor for the operator. Therefore, the present inventors devised that an imitated object which imitates a contour of an object to be handled by a slave arm is used as a master device, instead of a master arm, or an end effector attached to a hand part of the master arm.

According to one aspect of the present disclosure, a remote control robot system includes a slave arm, a master main body imitating the shape of an object handled by the slave arm, a manipulation receiving device configured to receive manipulation of an operator based on the position and posture of the master main body, and a control device configured to control operation of the slave arm based on the manipulation received by the manipulation receiving device so that behavior of the object corresponds to behavior of the master main body.

According to the remote control robot system, the operator is able to move the master main body to cause the slave arm to operate. That is, when the operator handles the master main body as if he/she handles the object, the slave arm operates so that the behavior of the object corresponds to the behavior of the master main body. Therefore, the operator is able to instinctively operate the slave arm using the master device.

Effect of the Disclosure

According to the remote control robot system of the present disclosure, the operator is able to instinctively operate the slave arm by using the master device.

MODES FOR CARRYING OUT THE DISCLOSURE

Hereinafter, embodiments of the present disclosure will be described with reference to the accompanying drawings.
[Remote Control Robot System 100]

Figure 1:
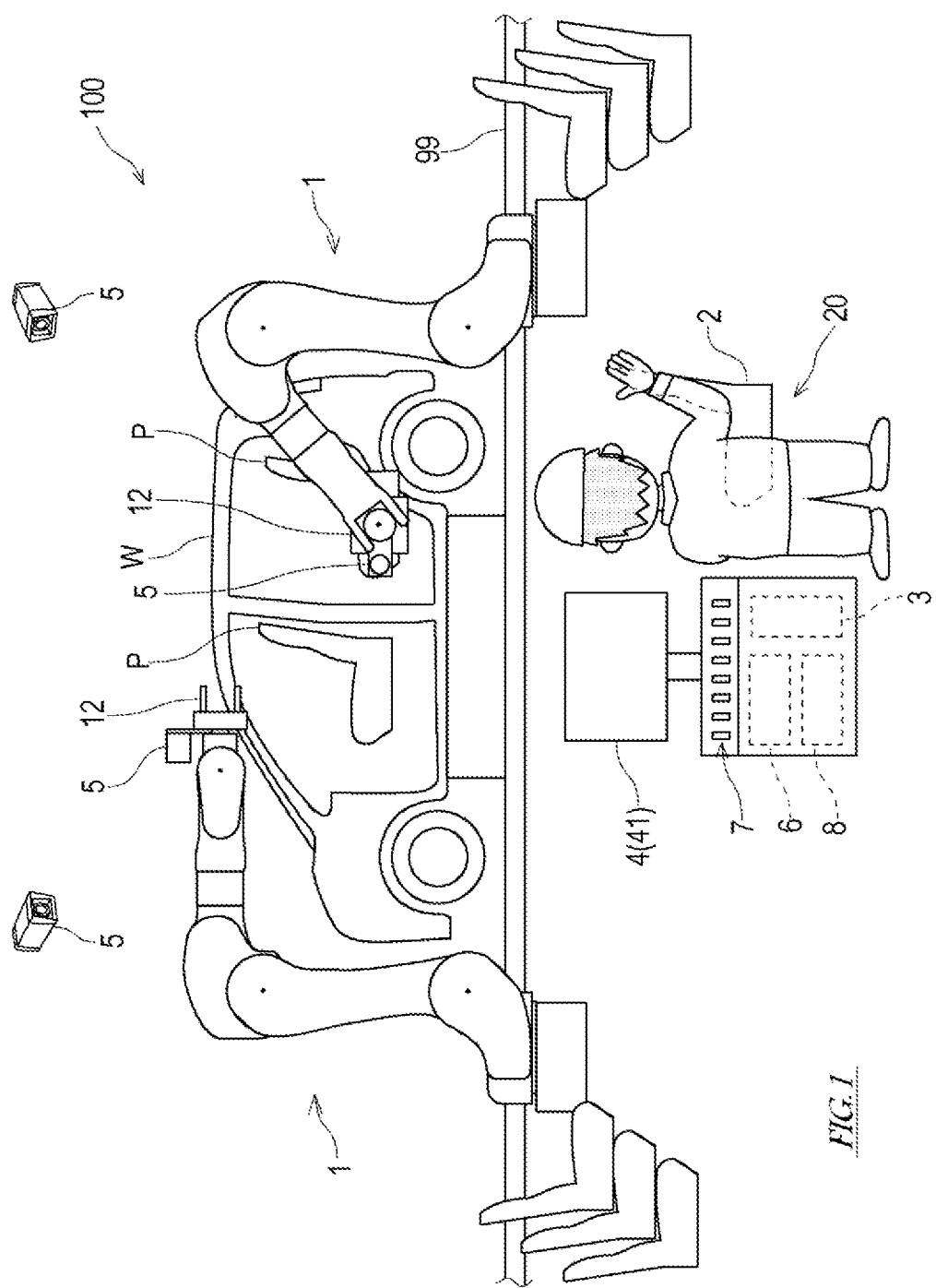
FIG. 1 is a view illustrating a situation of an automobile assembly line into which a remote control robot system according to one embodiment of the present disclosure is introduced.
Figure 2:
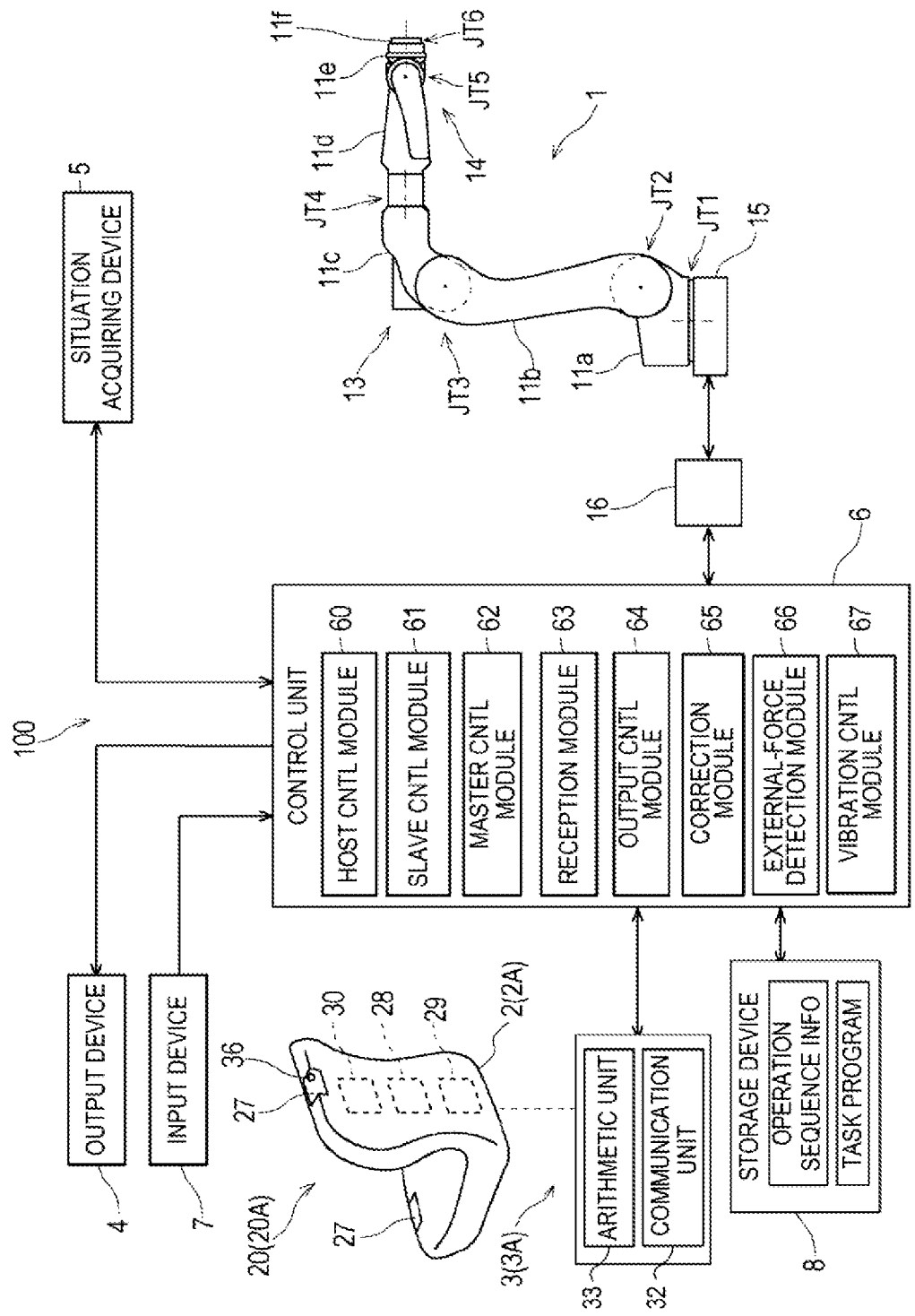
FIG. 2 is a block diagram schematically illustrating a configuration of the remote control robot system provided with a master device according to a first embodiment.

FIG. 1 is a view illustrating a situation of an automobile assembly line provided with a remote control robot system 100 according to one embodiment of the present disclosure, and FIG. 2 is a block diagram schematically illustrating a configuration of the remote control robot system 100. As illustrated in FIGS. 1 and 2, the remote control robot system 100 is a master-slave type robot system, and includes a slave arm 1, a master device 20, an input device 7, an output device 4, a situation acquiring device 5, and a control unit 6 which comprehensively controls the system 100.

In FIG. 1, illustrated is the automobile assembly line including a conveyor line of workpieces formed by a conveyor 99 in a workspace, the slave arm 1 installed along the conveyor line, and the master device 20 installed at the position distant from workspace (outside of the workspace). In this automobile assembly line, the slave arm 1 performs a work to carry a seat P, which is one example of a component, into a vehicle body W which is the workpiece. In the following description, the seat P is defined as an object to be handled by the slave arm 1. Note that the object is not limited to the seat P, but it may be widely applied to those to be handled by the slave arm 1 (in more detail, an end effector 12 of the slave arm 1). Moreover, the remote control robot system 100 according to the present disclosure is not limited to such an automobile assembly line, but it may be widely applied to various kinds of production facilities.

The slave arm 1 according to this embodiment has three control modes of an automatic mode, a manual mode, and a correctable automatic mode. The control mode of the slave arm 1 is switchable so that operation is controlled by one selected from these plurality of control modes.

A control mode in which the slave arm 1 is operated according to a preset task program is herein referred to as "the automatic mode." In the automatic mode, the slave arm 1 automatically performs a given work without manipulation of the master device 20 by an operator, similar to a conventional teaching playback robot.

Moreover, a control mode in which the slave arm 1 is operated based on the operator's manipulation received by the master device 20 is herein referred to as "the manual mode." The master device 20 is capable of receiving manipulation inputted by the operator directly moving the master device 20. Note that, in the manual mode, the operator's manipulation received by the master device 20, and the motion of the slave arm 1 which is operating based on the manipulation may be corrected automatically.

Moreover, a control mode in which the slave arm 1 is operated according to the preset task program while being corrected by the operator's manipulation received by the master device 20 as required is herein referred to as "the correctable automatic mode." In the correctable automatic mode, the motion of the slave arm 1 which is operating according to the preset task program is corrected based on the operator's manipulation received by the master device 20.

Below, each component of the remote control robot system 100 is described in detail.

[Slave Arm 1]

In FIG. 1, two slave arms 1 are illustrated, which are installed parallel to the conveyor line of the workpiece and separated from each other. The two slave arms 1 are vertical articulated robots, and they have substantially the same structure other than the end effector 12. Note that the master device 20 may be configured to be capable of manipulating one slave arm 1, or may be configured to be capable of manipulating a plurality of (two or more) slave arms 1. Here, in order to simplify the description, the master device 20 is configured to be capable of manipulating one slave arm 1.

As illustrated in FIG. 2, the slave arm 1 is an articulated robot arm having a plurality of joints JT1-JT6, which is comprised of a coupled body of a plurality of links 11a-11f, and a pedestal 15 which supports the coupled body. In more detail, at the first joint JT1, the pedestal 15 and a base-end part of the first link 11a are coupled to each other so as to be rotatable about an axis extending vertically. At the second joint JT2, a tip-end part of the first link 11a and a base-end part of the second link 11b are coupled to each other so as to be rotatable about an axis extending horizontally. At the third joint JT3, a tip-end part of the second link 11b and a base-end part of the third link 11c are coupled to each other so as to be rotatable about an axis extending horizontally. At the fourth joint JT4, a tip-end part of the third link 11c and a base-end part of the fourth link 11d are coupled to each other so as to be rotatable about an axis extending in the longitudinal directions of the fourth link 11d. At the fifth joint JT5, a tip-end part of the fourth link 11d and a base-end part of the fifth link 11e are coupled to each other so as to be rotatable about an axis perpendicular to the longitudinal directions of the fourth link 11d. At the sixth joint JT6, a tip-end part of the fifth link 11e and a base-end part of the sixth link 11f are coupled to each other so as to be twistable and rotatable. A mechanical interface is provided to a tip-end part of the sixth link 11f. The end effector 12 (see FIG. 1) corresponding to the contents of work is mounted to the mechanical interface attachably and detachably.

Figure 3:
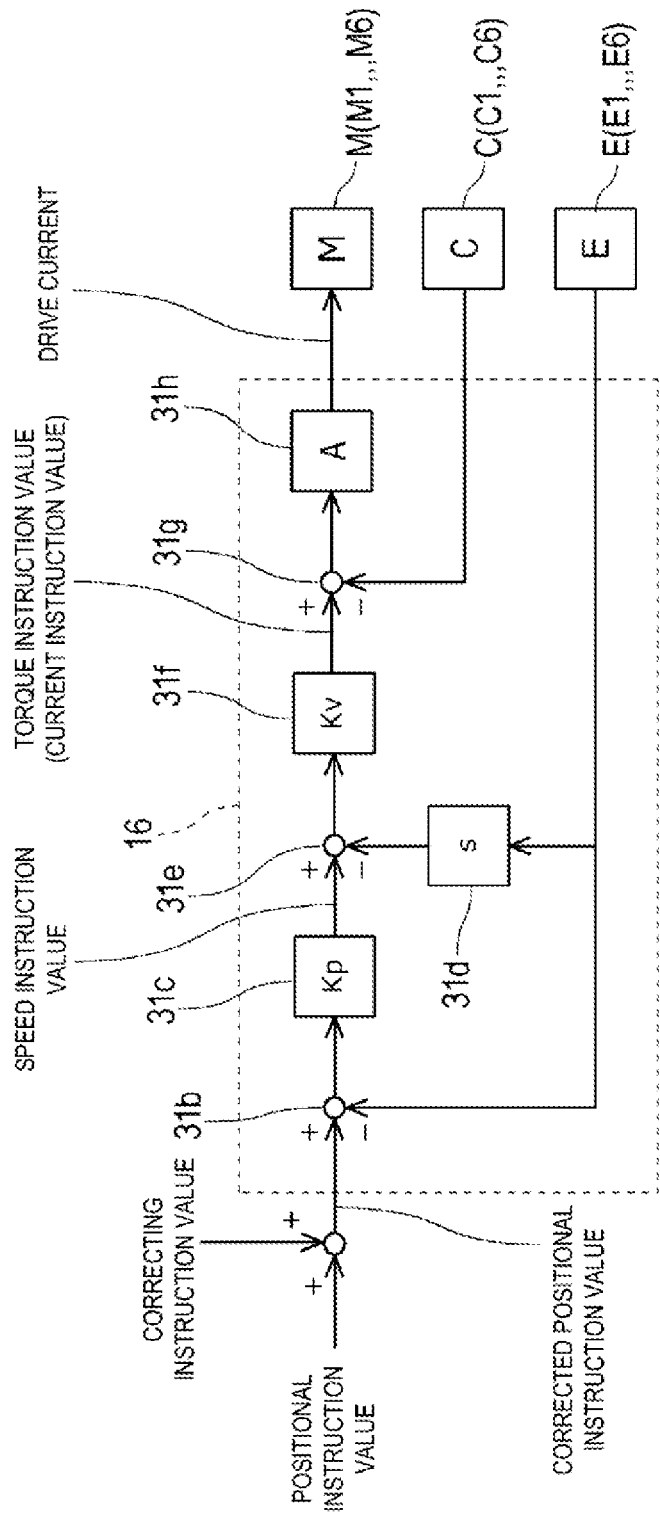
FIG. 3 is a block diagram illustrating a configuration of a control system of a slave arm.

FIG. 3 is a block diagram illustrating a configuration of a control system of the slave arm 1. In this figure, a concrete electric configuration focusing on a motor controller 16 is illustrated. As illustrated in FIG. 3, drive motors M1-M6 are provided to the joints JT1-JT6 of the slave arm 1, respectively, each of which is one example of an actuator which relatively rotates two members connected by the joint. The drive motors M1-M6 are, for example, servo motors which are servo-controlled by the motor controller 16. Moreover, the drive motors M1-M6 are provided with position sensors E1-E6 which detect rotational positions of the drive motors M1-M6, and current sensors C1-C6 which detect current for controlling the rotations of the drive motors M1-M6, respectively. The position sensors E1-E6 may be those capable of detecting rotational positions, such as encoders, resolvers, and pulse generators, for example. Note that, in the description of the drive motors M1-M6, the position sensors E1-E6, and the current sensors C1-C6, 1-6 of the suffixes are given to the alphabet corresponding to the respective joints JT1-JT6. Below, when an arbitrary joint is illustrated among the joints JT1-JT6, the suffix is omitted and it is referred to as "JT," and the same is applied to the drive motor M, the position sensor E, and the current sensor C.

The drive motor M, the position sensor E, and the current sensor C are electrically connected with the motor controller 16. Although the motor controller 16 according to this embodiment is capable of servo-controlling the plurality of drive motors M alone, the motor controllers may be provided corresponding to the respective drive motors M.

The motor controller 16 generates a drive instruction value (a current instruction value) based on a positional instruction value, a servo gain, etc. which are acquired from the control unit 6 described later (in more detail, a slave control module 61), and supplies the drive current corresponding to the drive instruction value to the drive motor M. An output rotational angle of the drive motor M is detected by the position sensor E, and is fed back to the motor controller 16. Note that the functions of the motor controller 16 and the slave control module 61 may be implemented by a single circuit or a single arithmetic device.

When the positional instruction value is inputted into the motor controller 16 from the control unit 6 (in more detail, the slave control module 61), the inputted positional instruction value is given to the plus-side input of a subtractor 31b. A signal indicative of the rotational angle detected by the position sensor E (a present position value) is given to the minus-side input of the subtractor 31b. The subtractor 31b subtracts the rotational angle from the positional instruction value. The output of the subtractor 31b is given to a coefficient multiplier 31c, where the output is amplified with a position gain Kp, and is then given to the + input of a subtractor 31e. The resultant obtained by a differentiator 31d differentiating the rotational angle from the position sensor E is given to the − input of the subtractor 31e. The output of the subtractor 31e is given to a coefficient multiplier 31f, where the output is amplified with a speed gain Kv, and is then given to the + input of a subtractor 31g. A current value from the current sensor C is given to the − input of the subtractor 31g. The subtracted output of the subtractor 31g is inputted into an amplifier circuit 31h as the drive instruction value, and the drive current corresponding to the amplified drive instruction value is supplied to the drive motor M.

[Master Device 20]

The master device 20 is a means for receiving the operator's manipulation. The master device 20 is comprised of a master main body 2 which imitates the shape of the object to be handled by the slave arm 1, and a manipulation receiving device 3 which receives the manipulation given to the master main body 2 based on the position and posture of the master main body 2.

A vibration motor 30 is mounted to the master main body 2. The vibration motor 30 is comprised of, for example, a motor, and a weight fixed to an output shaft of the motor. In such a vibration motor 30, vibration is generated when the motor rotates, because an eccentricity of the center-of-gravity of the weight. The vibration generated by the vibration motor 30 is transmitted to the master main body 2 to vibrate the master main body 2. Note that the drive electric power of the vibration motor 30 is supplied from a battery (not illustrated) mounted to the master main body 2.

In the remote control robot system 100 according to this embodiment, the slave arm 1 operates in the manual mode and the correctable automatic mode, so that the object (e.g., the seat P) held by the slave arm 1 behaves corresponding the behavior of the master main body 2. That is, the slave arm 1 operates so that changes in the position and posture of the object held by the slave arm 1 correspond to changes in the position and posture of the master main body 2 (e.g., become identical or similar in the position and posture). The master device 20 will be described later in detail.

[Input Device 7]

The input device 7 is an input means which is installed outside the workspace, together with the master device 20, receives manipulating instructions from the operator, and inputs the received manipulating instructions into the control unit 6. Into the input device 7, operations other than the operation according to the position and posture of the slave arm 1 are inputted. The input device 7 is provided with one or more operational input tools which input operational instructions other than the position and posture of the slave arm 1, such as an operational input tool for selecting the control mode of the slave arm 1, and an emergency stop switch. The one or more operational input tools may include, for example, a known operational input tool, such as a touch panel, a key, a lever, a button, a switch, a dial plate, etc. Moreover, a mobile terminal, such as a programmable display device (pendant) or a tablet computer, may be used as the input device 7.

[Situation Acquiring Device 5]

The situation acquiring device 5 is a means for acquiring situation information indicative of a situation of the slave arm 1 in the workspace. The situation information includes information utilized in order to recognize the position, the posture and the like of the slave arm 1 in the workspace, or the situation around the slave arm 1. More specifically, the situation information includes, for example, information required for enabling recognition of the situation of the slave arm 1 in the workspace and the situation around the slave arm 1, such as the position and posture of the slave arm 1 in the workspace, a spatial relationship between the slave arm 1 and the workpiece, or a spatial relationship between the slave arm 1 and an assembled component to which the assembling component is assembled.

The situation acquiring device 5 is implementable by, for example, a sensor, an imaging device (camera), a communication device, an encoder, etc. The sensor may include, for example, a laser sensor, a radar sensor or the like which measures a distance to or a position of the assembling component or the assembled component. Further, it may also include a stereoscopic camera which is a sensor for measuring a distance from the slave arm 1 to an object around the slave arm 1 by using image data obtained from a plurality of imaging devices. The communication device may include, for example, a communication device which acquires information from the assembling component or the assembled component, or a sensor and an imaging device installed at given positions in the workspace. The encoder may include, for example, an encoder capable of detecting an amount of movement or the position of the slave arm 1.

The situation acquiring device 5 acquires the situation information as required, and the acquired situation information is inputted into the control unit 6 described later where it is used for the motion control of the slave arm 1. Further, the control unit 6 may also be configured to control the output device 4 to output the situation information. The situation acquiring device 5 may be attached to the slave arm 1, or may be attached at a suitable position in the workspace. Moreover, the number of situation acquiring devices 5 attached may be one, or may be plural. The attaching position and number are arbitrary, as long as that a suitable number of situation acquiring devices 5 are attached to positions from which the situation information can appropriately be acquired.

[Output Device 4]

The output device 4 is to output the information transmitted from the control unit 6. The output device 4 is installed at a position which is easily and visually recognizable by the operator who is operating the master main body 2. The output device 4 includes at least a display device 41, and may further include a printer, a speaker, a hazard light, etc. The display device 41 displays and outputs the information transmitted from the control unit 6. For example, the speaker outputs the information transmitted from the control unit 6 as sound. Moreover, for example, the printer prints output the information transmitted from the control unit 6 on recording media, such as paper.

[Storage Device 8]

The storage device 8 stores various task programs used for the control of the slave arm 1. The task program may be created as an operational flow of each work. For example, the task program is created by teaching, and is stored in the storage device 8 so as to be associated with identification information and a task of the slave arm 1. Note that, although the storage device 8 is described as independent from the control unit 6, a storage device provided to the control unit 6 may function as the storage device 8.

Moreover, the storage device 8 stores operation sequence information created beforehand. The operation sequence information is information related to the operation sequence which defines a series of work processes to be carried out by the slave arm 1 in the workspace. In this operation sequence information, the operating order of the work processes is associated with the control mode of the slave arm 1. Moreover, in this operation sequence information, each work process is associated with the task program for causing the slave arm 1 to automatically perform the work. Note that the operation sequence information may include, for each work process, the program for causing the slave arm 1 to automatically perform the work.

[Control Unit 6]

As illustrated in FIG. 2, the slave arm 1, the master device 20, the output device 4, the situation acquiring device 5, the input device 7, and the storage device 8 are communicatably connected to the control unit 6 wiredly or wirelessly.

The control unit 6 is a so-called computer, and has an arithmetic processor, such as a CPU, and a memory part, such as a ROM and a RAM, (none of them is illustrated). The memory part stores the control program executed by the control unit 6, various fixed data, etc. The arithmetic processor performs, for example, transmission and reception of data with external devices, such as the input device 7, the output device 4, and the storage device 8. Moreover, the arithmetic processor performs inputs of detection signals from various sensors and outputs control signals to respective controlled objects. In the control unit 6, the arithmetic processor reads and executes software, such as the program stored in the memory part to perform processing for controlling various operations of the system 100. Note that the control unit 6 may execute each processing by a centralized control with a single computer, or may execute each processing by a distributed control with a plurality of collaborating computers. Moreover, the control unit 6 may be comprised of a microcontroller, a programmable logic controller (PLC), etc.

The control unit 6 is provided with a host control module 60, the slave control module 61, a master control module 62 that controls manipulation of the master device 20, a reception module 63, an output control module 64, a correction module 65, an external-force detection module 66, and a vibration control module 67 as a functional block. In FIG. 2, although these functional blocks are collectively illustrated by a single control unit 6, each functional block or a combination of a plurality of functional blocks may be implemented by one or more independent computers. In this case, some of these functional blocks may be disposed in the workspace, and the rest may be disposed outside the workspace.

The slave control module 61 controls the operation of the slave arm 1. In the automatic mode, the slave control module 61 reads the task program stored in the storage device 8, generates the positional instruction value according to the task program, and gives the positional instruction value, the servo gain, etc. to the motor controller 16 of the slave arm 1. Moreover, in the manual mode, the slave control module 61 generates the positional instruction value based on manipulating information accepted by the master device 20 and received by the reception module 63, and gives the positional instruction value, the servo gain, etc. to the motor controller 16 of the slave arm 1. Moreover, in the correctable automatic mode, the slave control module 61 reads the task program stored in the storage device 8, generates the positional instruction value (or the corrected positional instruction value) based on the task program and a correcting instruction value acquired from the correction module 65, and gives the positional instruction value, a servo gain, etc. to the motor controller 16 (see FIG. 3). Note that, in the correctable automatic mode, the correcting instruction value is calculated as zero unless the correcting instruction value is given from the correction module 65.

The reception module 63 receives an input signal transmitted from the outside of the control unit 6. The input signal received by the reception module 63 includes, for example, the signal transmitted from the master device 20, the signal transmitted from the input device 7, the signal indicative of the situation information transmitted from the situation acquiring device 5, etc.

The output control module 64 controls the output device 4 to output from the output device 4 information to be notified to the operator. For example, the output device 4 outputs to the display device 41 information for identifying a target slave arm 1, and information for urging the input of selection of the control mode of the slave arm 1, when starting a selected portion of the operation sequence. Moreover, for example, the output device 4 outputs to the display device 41 the situation information and operating situation of the slave arm 1 which is manipulated by the master device 20, when the control modes of the slave arm 1 is the manual mode or the correctable automatic mode. Moreover, for example, the output device 4 outputs an alarm to the speaker or the display device 41, when a failure occurs to the system 100.

The correction module 65 corrects the motion of the slave arm 1 based on the manipulation received by the master device 20, when the control mode of the slave arm 1 is the correctable automatic mode. For example, when the position and posture of the master main body 2 change by the operator moving the master main body 2, the master device 20 receives the displacements of the position and posture as correcting instructions, and inputs them into the control unit 6. When the control mode of the slave arm 1 is the correctable automatic mode and the reception module 63 receives a correcting instruction signal, the correction module 65 generates the correcting instruction value based on the correcting instruction signal. An equation or map for obtaining the correcting instruction value from the correcting instruction signal is stored beforehand. Such a correcting instruction value may be, for example, a value proportional to the amount of change in the position and posture of the master main body 2. The generated correcting instruction value is transmitted to the slave control module 61, and the positional instruction value corrected from the slave control module 61 is outputted to the motor controller 16 (see FIG. 3).

The external-force detection module 66 detects an external force which the slave arm 1 received from environment, when the control mode of the slave arm 1 is the manual mode or the correctable automatic mode. The external-force detection module 66 according to this embodiment detects an error of the displacements of the position and posture of the slave arm 1 from the corresponding displacements of the position and posture of the master main body 2, as the external force which the slave arm 1 received from environment. Note that, the displacements of the position and posture of the master main body 2 may be calculated based on the information acquired from the manipulation receiving device 3. Moreover, the displacements of the position and posture of the slave arm 1 may be calculated based on the rotational position of each joint JT which the control unit 6 or the motor controller 16 acquired from the position sensor E. The external-force detection module 66 gives the calculated external force to the vibration control module 67.

The vibration control module 67 outputs a drive signal to the vibration motor 30 based on the external force calculated by the external-force detection module 66 to operate the vibration motor 30 mounted to the master main body 2. Although the drive signal to the vibration motor 30 is outputted to the master main body 2 through the manipulation receiving device 3 in this embodiment, it may be wirelessly outputted to the master main body 2 from the control unit 6.

The vibration control module 67 does not cause the vibration motor 30 to vibrate when the external force is below a given threshold value. That is, the vibration control module 67 does not output the drive signal to the vibration motor 30 when the external force is below the given threshold value. Moreover, when the external force exceeds the given threshold value, the vibration control module 67 outputs the drive signal to the vibration motor 30 (i.e., the master main body 2) to cause the vibration motor 30 to vibrate at a rotational speed proportional to the magnitude of the external force. As the rotational speed of the vibration motor 30 increases, the amplitude becomes larger so that the master main body 2 is vibrated more greatly. Thus, the operator manipulating the master main body 2 is able to perceive the existence of the external force which the slave arm 1 received from environment, and its magnitude by the vibration of the master main body 2.

The host control module 60 reads the operation sequence information stored in the storage device 8, and outputs instructions to the slave control module 61, the master control module 62, the output control module 64, the correction module 65, the external-force detection module 66, and the vibration control module 67 so that the slave arm 1, the master device 20, the output device 4, and the situation acquiring device 5 operate in accordance with the operation sequence information.

[Operation of Remote Control Robot System 100]

Next, one example of operation of the remote control robot system 100 having the above configuration is described. Here, an operational flow of the system 100 is described for a case where the remote control robot system 100 is established as the automobile assembly line, and is applied to one example in which the slave arm 1 is made to perform a work to attach a seat to an automobile body. Note that the remote control robot system 100 according to the present disclosure is not limited to such an automobile assembly line, but it may be widely applied to various production facilities.

The operation sequence information on the seat attachment work to the automobile body stored in the storage device 8 is comprised of a component extraction task T1 in which a seat is extracted from a container, a component delivery task T2 in which the seat is delivered to near an attachment position of the body, and a component attachment task T3 in which the seat near the attachment position is attached to the attachment position, and these tasks T1-T3 are repeatedly performed in this order. The component extraction task T1 and the component delivery task T2 among the operation sequence are "automatic portions" in which the slave arm 1 operates in the automatic mode. The automatic portion of the operation sequence is associated with the automatic mode as the control mode. Moreover, the component attachment task T3 among the operation sequence is a "selected portion" in which the slave arm 1 operates in the control mode selected from the automatic mode, the manual mode, and the correctable automatic mode. The selected portion of the operation sequence is not associated with a specific control mode, and the control mode is selectable.

First, the control unit 6 reads the given operation sequence information stored in the storage device 8, and starts the control of the system 100 in accordance with the operation sequence information.

According to the example of the operation sequence of the seat attachment work to the automobile body, the control unit 6 first reads the task program of the component extraction task T1 from the storage device 8 and executes the task program. Next, the control unit 6 reads and executes the task program of the component delivery task T2. In the component extraction task T1 and the component delivery task T2, the control unit 6 controls the operation of the slave arm 1 in the automatic mode.

Once the component delivery task T2 is finished, the control unit 6 displays on the display device 41 a selection screen for urging the operator a selection of the control mode for the subsequent component attachment task T3. The control unit 6 also outputs to the display device 41 the situation information of the slave arm 1 for which the control mode is going to be selected. Here, the situation information displayed on and outputted to the display device 41 may include the identification information on the slave arm 1 currently displayed, the contents of process to be performed subsequently, etc.

The operator visually checks the situation s information of the slave arm 1 displayed on the display device 41, and selects one of the three control modes. The selection of the control mode by the operator is received by the master device 20 or the input device 7, and it is inputted into the control unit 6.

In the above situation, when the automatic mode is selected, the control unit 6 reads the task program of the component attachment task T3 from the storage device 8, and controls the operation of the slave arm 1 in the automatic mode. Moreover, when the manual mode is selected, the control unit 6 controls the operation of the slave arm 1 in the manual mode. Alternatively, when the correctable automatic mode is selected, the control unit 6 controls the operation of the slave arm 1 in the correctable automatic mode.

In the above situation, when either one of the manual mode and the correctable automatic mode is selected, the control unit 6 causes the display device 41 to display and output the situation information of the slave arm 1 throughout the process. As described above, the control unit 6 advances the work process as required in accordance with the operation sequence.

Below, first to fourth embodiments of the master device 20 are described. In each embodiment, other than the master device 20, the rest of the configuration of the remote control robot system 100 is substantially the same. Moreover, in each embodiment, the configuration of the master device 20 is partially common. Therefore, in the following description, the same reference characters are given to the same or similar members in the drawings to omit redundant description.

First Embodiment

FIG. 2 is a block diagram schematically illustrating a configuration of the remote control robot system 100 provided with the master device 20 (20A) according to the first embodiment. As illustrated in FIG. 2, the master device 20A includes a master main body 2A and a manipulation receiving device 3A.

In this embodiment, an object to be handled by the slave arm 1 is a seat P of an automobile (see FIG. 1). Thus, the master main body 2 has a shape which imitates the contour of the object to be handled by the slave arm 1 (i.e., the seat P). Note that the contour of the master main body 2 is not limited to the shape same as the object, but may have a similar shape as the object. For example, for easier manipulation by the operator, the contour of the master main body 2 may be smaller than the object and may have the similar shape as the object.

As for the master main body 2, if its contour corresponds to the contour of the object to be handled by the slave arm 1, an internal structure, material, etc. does not need to correspond with those of the object. For example, the master main body 2 may be a foamed resin molded product or a hollow resin molded product. Such a master main body 2 is sufficiently lightweight so that it is easily manipulatable by the operator, even if it is a large-sized product. Note that the use of an identical product to the object as the master main body 2 shall not be precluded. If the identical product to the object is used as the master main body 2, cost and workloads to design and manufacture the master main body 2 can be reduced.

Further, a pair of gripping parts 27 are provided in the master main body 2, at positions corresponding to positions where the operator gripes when he/she handles the object (seat P) with both hands. Each gripping part 27 has, for example, a shaped portion, such as a handle, which is easy to be gripped by the operator.

An on/off switch 36 is provided to at least one of the gripping parts 27. Thus, by providing the on/off switch 36 to the gripping part 27, the operator is able to operate the on/off switch 36 while gripping the gripping part 27. Note that the on/off switch 36 may be a foot switch provided at the operator's feet. An on/off signal of the on/off switch 36 is outputted to the manipulation receiving device 3. The manipulation receiving device 3 receives operational instructions given to the master main body 2 based on the position and posture of the master main body 2, when the on/off switch 36 is ON.

Moreover, the manipulation receiving device 3A includes a motion sensor unit 28, a movable-side communication unit 29, a stationary-side communication unit 32, and an arithmetic unit 33. Among these, the motion sensor unit 28 and the movable-side communication unit 29 are mounted to the master main body 2A.

The motion sensor unit 28 includes at least an acceleration sensor and an angular-velocity sensor. Note that the motion sensor unit 28 is known, and description of the concrete structure thereof is omitted. The movable-side communication unit 29 wirelessly transmits and outputs to the stationary-side communication unit 32 detection data detected by each sensor mounted to the motion sensor unit 28. Moreover, the movable-side communication unit 29 wirelessly transmits and outputs to the stationary-side communication unit 32 the on/off signal of the on/off switch 36. Further, the movable-side communication unit 29 wirelessly receives the drive signal of the vibration motor 30 from the stationary-side communication unit 32.

The stationary-side communication unit 32 outputs the drive signal of the vibration motor 30 received from the control unit 6. Moreover, the stationary-side communication unit 32 receives detection information on the motion sensor unit 28 outputted from the movable-side communication unit 29 and the on/off signal of the on/off switch 36. The arithmetic unit 33 calculates the position and posture of the master main body 2 based on the information received by the communication unit 32. Note that, since the technique of calculating the position and posture of a moving object (i.e., the master main body 2) based on the acceleration information and the angular-velocity information which are detected by the motion sensor unit 28 is known, detailed description related to the contents of operation processing in the arithmetic unit 33 is omitted. The manipulation receiving device 3A is communicatably connected with the control unit 6, and the manipulation receiving device 3A inputs into the control unit 6 the manipulating information based on the calculated position and posture of the master main body 2.

As described above, the remote control robot system 100 according to this embodiment includes the slave arm 1, the master main body 2 which imitates the shape of the object to be handled by the slave arm 1, the manipulation receiving device 3 which receives the operator's manipulation based on the position and posture of the master main body 2, and the control unit 6 (in detail, the slave control module 61) which controls the operation of the slave arm 1 based on the manipulation received by the manipulation receiving device 3 so that the behavior of the object corresponds to the behavior of the master main body 2.

According to the remote control robot system 100 of the configuration, the operator is able to move the master main body 2 which imitates the shape of the object to cause the slave arm 1 to operate. That is, when the operator handles the master main body 2 as if he/she handles the object, the slave arm 1 operates so that the behavior of the object corresponds to the behavior of the master main body 2. For example, when the operator moves the master main body 2 which imitates the seat P as if he/she arranges it inside the automobile body W, the slave arm 1 operates so that the seat P held by the slave arm 1 is arranged inside the automobile body W. Therefore, the operator is able to instinctively operate the slave arm 1 using the master device 20.

Especially, the manipulation receiving device 3A according to this embodiment includes the motion sensor unit 28 mounted to the master main body 2A, and the arithmetic unit 33 which calculates the position and posture of the master main body 2 based on the information detected by the motion sensor unit 28.

Thus, since the manipulation receiving device 3A of the master device 20A utilizes the technology of the motion sensor, the master main body 2A is not fixed but has portability. The operator is able to move the master main body 2A within an area where the communication units 29 and 32 are communicatable, to manipulate the master main body 2A.

Moreover, in the remote control robot system 100 according to the embodiment, the master main body 2 is provided with the pair of gripping parts 27 at the positions corresponding to the positions where the operator grips when he/she handles with both hands the object to be handled by the slave arm 1.

Thus, the operator is able to grasp these gripping parts 27 and stably manipulate the master main body 2.

Moreover, the remote control robot system 100 according to the embodiment further includes the vibration motor 30 mounted to the master main body 2, the external-force detection module 66 (external-force detecting device) which detects the external force which the slave arm 1 received from environment, and the vibration control module 67 (vibration controlling device) which operates the vibration motor 30 so that the external force detected by the external-force detection module 66 is presented to the operator as the vibration of the master main body 2. Here, the vibration control module 67 operates the vibration motor 30 at the rotational speed proportional to the magnitude of the external force detected by the external-force detection module 66.

Thus, by presenting to the operator the external force detected by the external-force detection module 66 and its magnitude as the vibration of the master main body 2, the operator who perceived the vibration is able to take measures, such as decelerating the movement of the master main body 2.

Moreover, the remote control robot system 100 according to the embodiment further includes the storage device 8 which stores the task program. The slave arm 1 has the plurality of control modes of the automatic mode in which it is operated based on the task program stored beforehand, the manual mode in which it is operated based on the operator's manipulation which the manipulation receiving device 3 received, and the correctable automatic mode in which it is operated based on the task program while being corrected as required by the operator's manipulation which the manipulation receiving device 3 received. The control unit 6 (in detail, the slave control module 61) operates the slave arm 1 in one selected from the plurality of control modes.

According to this, the operator is able to select the control mode of the slave arm 1 from the automatic mode, the manual mode, and the correctable automatic mode according to the contents of work and the situation of the slave arm 1. The selection of the control mode may be performed based on a judgment of the operator. For example, works, such as gripping of a vulnerable component, precise fitting, exact positioning, and axial alignment, are preferably be performed in the manual mode or the correctable automatic mode in which the operator's manipulation is capable of being reflected in the motion of the slave arm 1. In such works, for example, if a failure is expected to occur when the slave arm 1 is completely operated automatically, the correctable automatic mode may be selected. Since, in the correctable automatic mode, the automatic operation of the slave arm 1 is the basis of operation and the operation is correctable by the operator's manipulation, the operator's load is small as compared with the manual mode and, thus, the lowering of the work efficiency can be controlled. Thus, according to this system 100, by the operator selecting the suitable control mode according to the situation from the plurality of control modes for each work, the non-stopping robot system is implementable.

Second Embodiment

Figure 4:
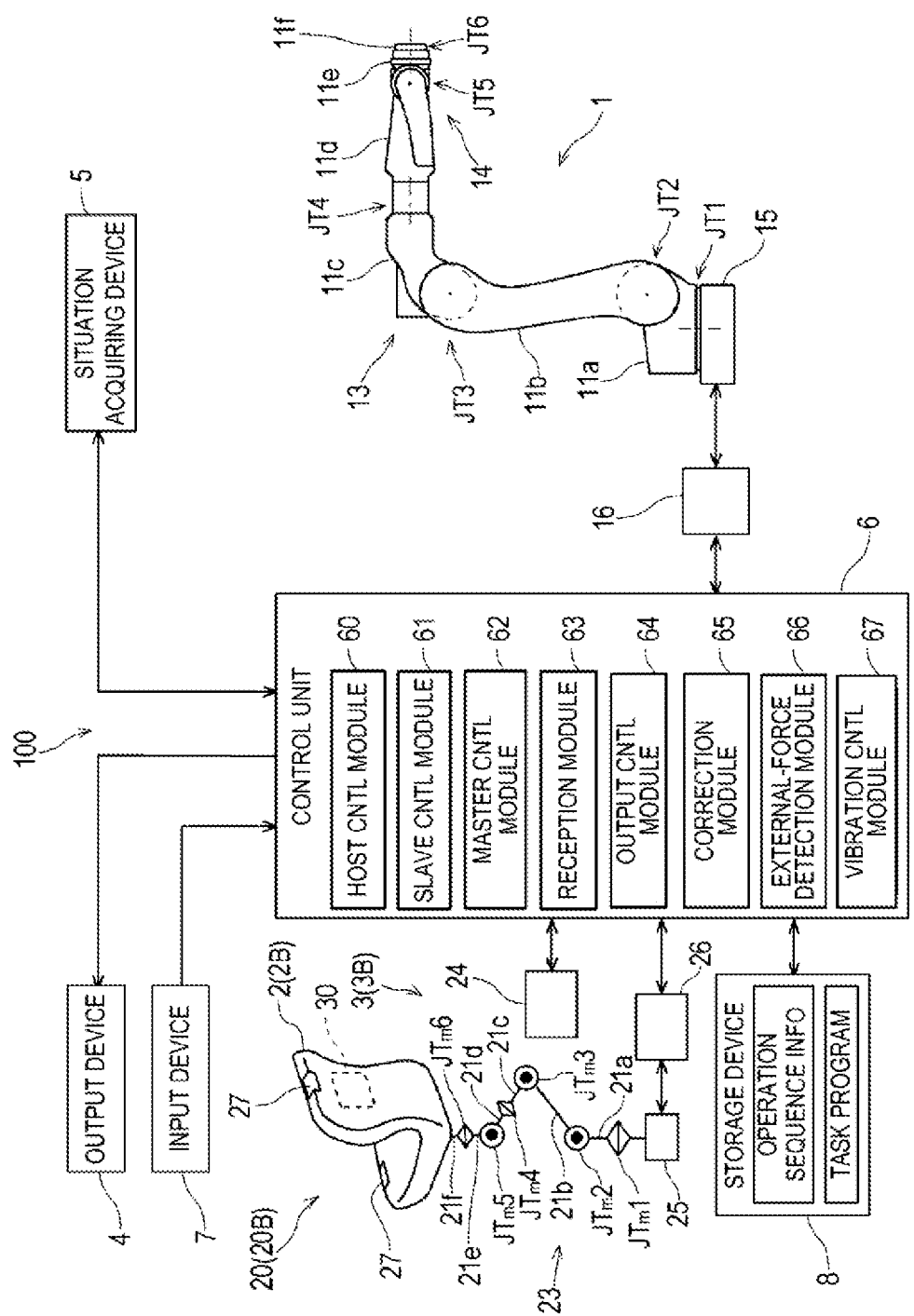
FIG. 4 is a block diagram schematically illustrating a configuration of the remote control robot system provided with a master device according to a second embodiment.

FIG. 4 is a block diagram schematically illustrating a configuration of the remote control robot system 100 provided with the master device 20 (20B) according to a second embodiment. As illustrated in FIG. 4, the master device 20B according to this embodiment includes a master main body 2B and a manipulation receiving device 3B. The configuration of the master main body 2B is substantially the same as that of the master main body 2A according to the first embodiment and, thus, detailed description thereof is omitted.

The manipulation receiving device 3B includes a manipulator 23 to which the master main body 2B is attached at a hand part thereof, and an arithmetic unit 24 which calculates the position and posture of the master main body 2B based on the rotational position of each joint of the manipulator 23.

The manipulator 23 is an articulated robot arm having a plurality of joints JTm1-JTm6 of which the number is the same as the slave arm 1, and is structured by serially coupling a pedestal 25 and a plurality of links 21a-21f. The coupling structure of the links 21a-21f of the manipulator 23 is substantially the same as that of the links 11a-11f of the slave arm 1 and, thus, detailed description thereof is omitted. The master main body 2B is attached to a tip-end part of the sixth link 21f of the manipulator 23 (i.e., the hand part of the manipulator 23).

The joints JTm1-JTm6 are provided with drive motors Mm1-Mm6 (not illustrated), respectively, as one example of an actuator which relatively rotates two members connected by the joint. The drive motors Mm1-Mm6 are, for example, servo motors which are servo-controlled by a motor controller 26. Moreover, the drive motors Mm1-Mm6 are provided with position sensors Em1-Em6 (not illustrated) which detect rotational positions thereof and current sensors Cm1-Cm6 (not illustrated) which detect current for controlling the rotations, respectively. The position sensors Em1-Em6 are, for example, encoders.

Similar to the drive system of the slave arm 1 described above, the drive motors Mm1-Mm6, the position sensors Em1-Em6, and the current sensors Cm1-Cm6 are electrically connected with the motor controller 26. Although the motor controller 26 according to this embodiment is capable of servo-controlling the plurality of drive motors Mm1-Mm6 alone, the motor controllers may be provided corresponding to the respective drive motors Mm1-Mm6.

Similar to the motor controller 16 described above, the motor controller 26 generates drive instruction values (torque instruction values) based on the positional instruction values, a servo gain, etc. which are acquired from the control unit 6 (in detail, the master control module 62), and supplies drive current corresponding to the drive instruction values to the drive motors Mm1-Mm6. The output rotational angles of the drive motors Mm1-Mm6 are detected by the position sensors Em1-Em6, and are fed back to the motor controller 26. Note that the functions of the motor controller 26 and the master control module 62 may be implemented by a single circuit or a single arithmetic device.

The master control module 62 of the control unit 6 operates the manipulator 23 so that the manipulator 23 changes its movement or posture according to an external force which the operator gave to the master main body 2B. That is, the operator's manipulating force is assisted by the operation of the manipulator 23. Moreover, when the operator gives the external force to the master main body 2B, the master control module 62 may operate the manipulator 23 so that the hand part of the manipulator 23 moves along a given route.

The arithmetic unit 24 calculates the position and posture of the master main body 2B attached to the hand part of the manipulator 23 based on the output rotational angles of the drive motors Mm1-Mm6 detected by the position sensors Em1-Em6, when the on/off switch 36 is ON. The manipulation receiving device 3B is communicatably connected with the control unit 6, and the manipulation receiving device 3B inputs into the control unit 6 the manipulating information based on the calculated position and posture of the master main body 2.

As described above, in the remote control robot system 100 according to this embodiment, the manipulation receiving device 3B of the master device 20B has the manipulator 23 to which the master main body 2B is attached at the hand part thereof, and the arithmetic unit 24 which calculates the position and posture of the master main body 2B based on the rotational positions of the respective joints JTm1-JTm6 of the manipulator 23.

Thus, the master main body 2B is supported by the manipulator 23 by attaching the master main body 2B to the hand part of the manipulator 23. Therefore, since the operator does not need to support the load of the master main body 2B, the operator's manipulation of the master main body 2B is stabilized. Moreover, since the manipulator 23 is capable of assisting the manipulating force of the master main body 2B, the operability of the master main body 2B is improved.

Third Embodiment

Figure 5:
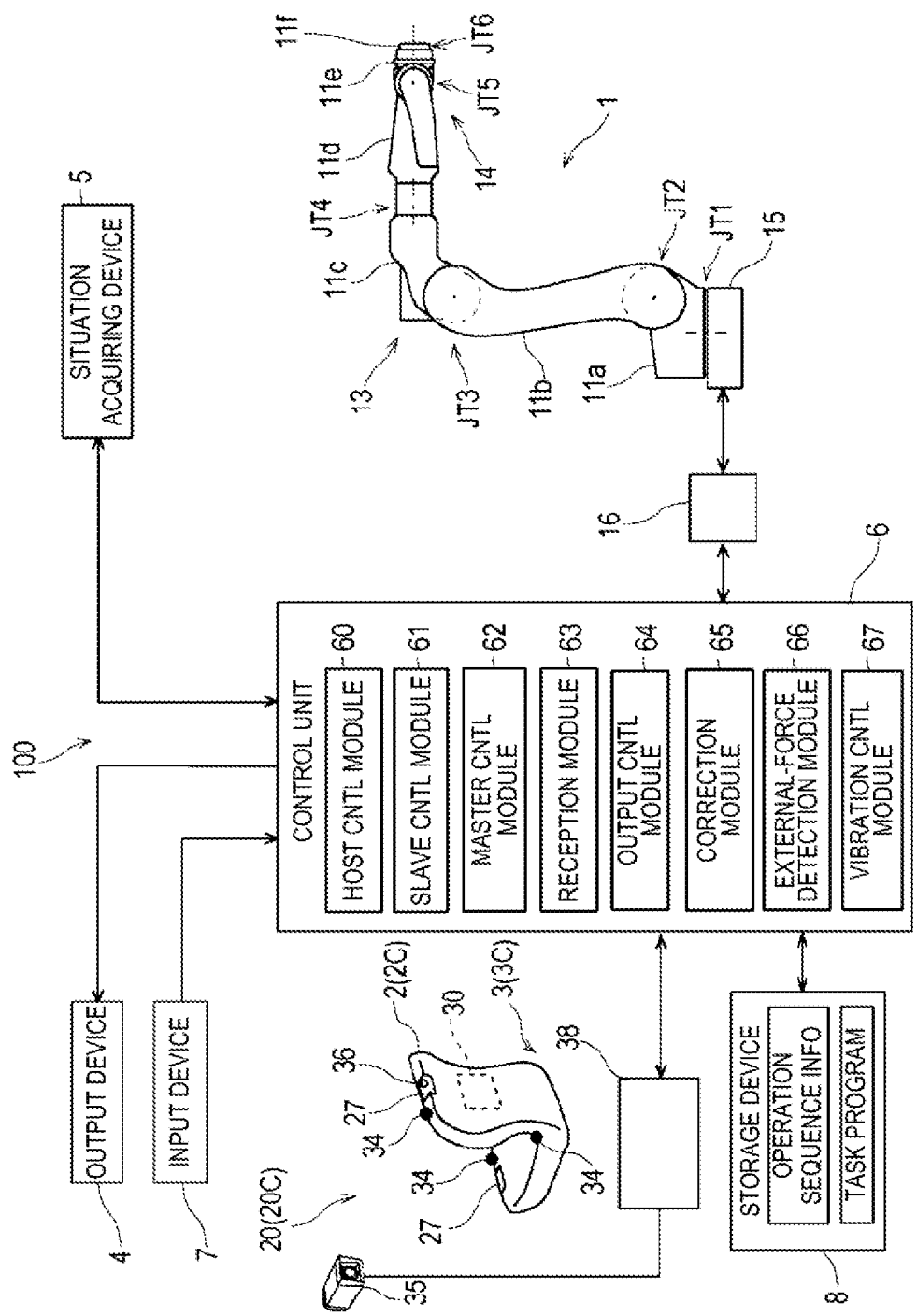
FIG. 5 is a block diagram schematically illustrating a configuration of the remote control robot system provided with a master device according to a third embodiment.

FIG. 5 is a block diagram schematically illustrating a configuration of the remote control robot system 100 provided with the master device 20 (20C) according to a third embodiment. As illustrated in FIG. 5, the master device 20C according to this embodiment includes a master main body 2C and a manipulation receiving device 3C. The configuration of the master main body 2C is substantially the same as that of the master main body 2A according to the first embodiment and, thus, detailed description thereof is omitted.

The manipulation receiving device 3C is configured as a motion capture system which captures a motion of the master main body 2C. Although various techniques are known for the motion capture system, for example, a motion capture system which is comprised of markers 34 provided at a plurality of locations on the surface of the master main body 2C, a plurality of camera devices 35 which image the markers 34, and an image-processing device 38 which processes the images obtained from these camera devices 35 to calculate the position and posture of the master main body 2C may be adopted. Alternatively, as the motion capture system, a motion capture system which is comprised of the camera devices 35 which image the master main body 2C, and the image-processing device 38 which processes the images obtained from these camera devices to calculate the position and posture of the master main body 2C may be adopted. Note that, since the motion capture system is known, the detailed description related to the structure or the contents of processing is omitted.

The manipulation receiving device 3C is communicatably connected with the control unit 6, and the manipulation receiving device 3C inputs into the control unit 6 the manipulating information based on the calculated position and posture of the master main body 2.

As described above, in the remote control robot system 100 according to this embodiment, the manipulation receiving device 3C of the master device 20C has a motion capture system including the camera devices 35 which images the master main body 2C or the plurality of markers 34 provided on the master main body 2C, and the image-processing device 38 which calculates the position and posture of the master main body 2C by processing the images imaged by the camera devices 35.

Thus, since the manipulation receiving device 3C of the master device 20C utilizes the motion capture technology, the master main body 2C has portability. In addition, the operator is able to move the master main body 2C in the area which is imageable by the camera devices 35 to manipulate the master main body 2C.

Fourth Embodiment

Figure 6:
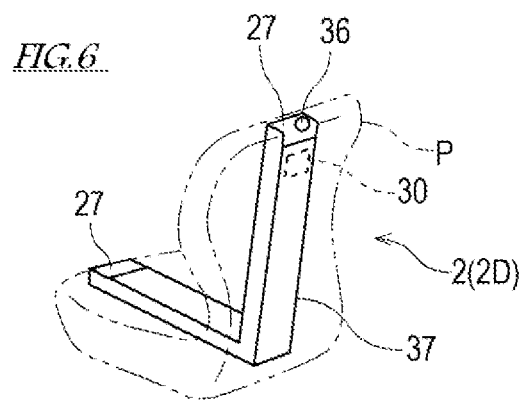
FIG. 6 is a schematic diagram of a master main body of a master device according to a fourth embodiment.

FIG. 6 is a schematic diagram of a master main body 2D of the master device 20 according to a fourth embodiment. As illustrated in FIG. 6, although the master main body 2D according to this embodiment imitates the shape of the object to be handled by the slave arm 1, the contour of the master main body 2D is not the same as or similar to the contour of the object.

The master main body 2D is comprised of the pair of gripping parts 27 provided at positions corresponding the positions where the operator grips with both hands when handling the object, and a rigid body 37 which connects the pair of gripping parts 27.

In this embodiment, the object to be handled by the slave arm 1 is the seat P, and the positions where the operator grips with both hands when handling the seat P are, for example, an upper part of a seat back and a tip-end part of a seating surface of the seat P. The pair of gripping parts 27 are provided with such a spatial relationship corresponding to these gripping positions. The rigid body 37 connects the pairs of gripping parts 27. In this embodiment, the gripping part 27 has an L-shape which imitates the L-shape of the seat P.

As described above, the master main body 2D according to this embodiment is formed with the pair of gripping parts 27, and the rigid body 37 which connects the pair of gripping parts 27.

The master main body 2D formed in this way is simply producible, while imitating the shape of the object to be handled by the slave arm 1. Therefore, cost and workloads related to the production of the master main body 2D can be reduced.

The suitable embodiments of the present disclosure are described above. It is apparent for a person skilled in the art that many improvements and other embodiments of the present disclosure are possible from the above description. Therefore, the above description is to be interpreted only as illustration, and it is provided in order to teach a person skilled in the art the best mode which implements the present disclosure. The details of the structures and/or functions of the present disclosure may be substantially changed without departing from the spirit of the present disclosure.

DESCRIPTION OF REFERENCE CHARACTERS

1: Slave Arm
2: Master Main Body
3: Manipulation Receiving Device
4: Output Device
5: Situation Acquiring Device
6: Control Unit
7: Input Device
8: Storage Device
11a-11f: Link
15: Pedestal
16: Motor Controller
20: Master Device
21a-21f: Link
25: Pedestal
26: Motor Controller
30: Vibration Motor
41: Display Device
60: Host Control Module
61: Slave Control Module (Slave Control Device)
62: Master Control Module (Master Control Device)
63: Reception Module
64: Output Control Module
65: Correction Module
66: External-force Detection Module (External-force Detecting Device)
67: Vibration Control Module (Vibration Controlling Device)
100: Remote Control Robot System

What is claimed is:

1. A remote control robot system, comprising:
a slave arm having a coupled body of a plurality of links and an end effector coupled to a tip-end part of the coupled body and configured to handle an object;
a master main body including a gripping part and an on/off switch provided to the gripping part, the master main body having a shape that corresponds to a shape of the object that is being held and delivered by the end effector of the slave arm;
a situation acquiring device configured to acquire situation information of the slave arm, the situation information containing a position and posture of the slave arm and a spatial relationship between the slave arm and the object;

a display device installed at a position which is visually recognizable by an operator who is operating the master main body, the display device being configured to display and output the situation information;

a manipulation receiving device configured to receive, based on changes in a position and posture of the master main body when the on/off switch is in an on state, manipulation given to the master main body in such a manner that while gripping the gripping part, the operator operates the on/off switch to directly move the master main body; and a control device configured to control operation of the slave arm based on the manipulation received by the manipulation receiving device so that changes in a position and posture of the object correspond to the changes in the position and posture of the master main body.

2. The remote control robot system of claim 1, wherein the manipulation receiving device includes:

a motion sensor unit mounted to the master main body; and an arithmetic unit configured to calculate the position and posture of the master main body based on information detected by the motion sensor unit.

3. The remote control robot system of claim 1, wherein the manipulation receiving device includes:

a manipulator to which the master main body is attached at a hand part thereof; and an arithmetic unit configured to calculate the position and posture of the master main body based on a rotational position of each joint of the manipulator.

4. The remote control robot system of claim 1, wherein the manipulation receiving device includes a motion capture system including camera devices configured to image the master main body or a plurality of markers provided on the master main body, and an image-processing device configured to calculate the position and posture of the master main body by processing the images captured by the camera devices.

5. The remote control robot system of claim 1, further comprising:

a vibration motor mounted to the master main body;

an external-force detecting device configured to detect an external force that the slave arm received from environment; and a vibration controlling device configured to operate the vibration motor so that the external force detected by the external-force detecting device is presented to the operator as vibration of the master main body.

6. The remote control robot system of claim 5, wherein the vibration controlling device operates the vibration motor at a rotational speed proportional to a magnitude of the external force detected by the external-force detecting device.

7. The remote control robot system of claim 1, wherein the gripping part of the master main body includes a pair of gripping parts at positions corresponding to positions where the operator grips when handling the object with both hands.

8. The remote control robot system of claim 7, wherein the master main body is formed with the pair of gripping parts and a rigid body connecting the pair of gripping parts.

* * * * *